United States Patent [19]

Arhancet

[11] Patent Number: 5,489,720
[45] Date of Patent: Feb. 6, 1996

[54] METHODS FOR INHIBITING VINYL AROMATIC MONOMER POLYMERIZATION

[75] Inventor: Graciela B. Arhancet, Katy, Tex.

[73] Assignee: Betz Laboratories, Inc., Trevose, Pa.

[21] Appl. No.: 269,307

[22] Filed: Jun. 30, 1994

[51] Int. Cl.⁶ .................................................. C07C 7/20
[52] U.S. Cl. .................................. 585/5; 585/4; 585/24
[58] Field of Search ................................. 585/4, 5, 24

[56] References Cited

U.S. PATENT DOCUMENTS

| | | |
|---|---|---|
| 2,965,685 | 12/1960 | Campbell .................................... 585/4 |
| 4,061,545 | 12/1977 | Watson et al. . | 
| 4,466,905 | 8/1984 | Butler et al. . |
| 4,720,566 | 1/1988 | Martin ...................................... 558/306 |
| 4,774,374 | 9/1988 | Abruscato et al. ...................... 585/24 |
| 4,929,778 | 5/1990 | Roling ......................................... 585/3 |

*Primary Examiner*—E. Rollins Cross
*Assistant Examiner*—E. D. Irzinski
*Attorney, Agent, or Firm*—Alexander D. Ricci; Philip H. Von Neida

[57] ABSTRACT

An improved method for inhibiting the polymerization of vinyl aromatic monomer with a hydroxylamine compound is disclosed. The improvement provides for adding a catalytic amount of a phenylenediamine compound to the vinyl aromatic system while replacing any phenylenediamine compound lost as a result of physical removal from the system via the waste stream.

8 Claims, 1 Drawing Sheet

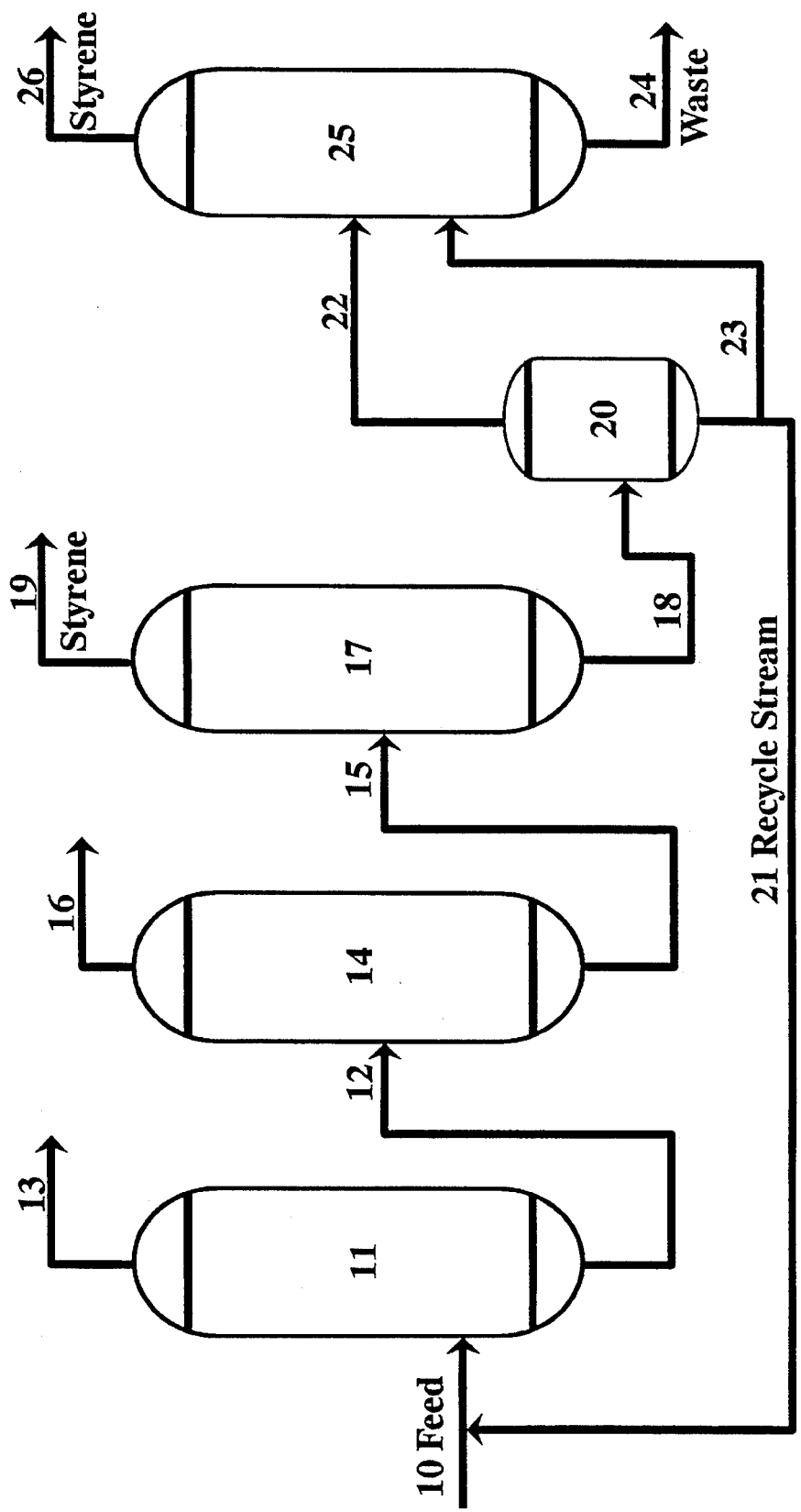
FIG. 1    Styrene Purification

//5,489,720

METHODS FOR INHIBITING VINYL AROMATIC MONOMER POLYMERIZATION

FIELD OF THE INVENTION

This invention relates to a novel method of inhibiting the polymerization of oxygen-free vinyl aromatic monomers utilizing a hydroxylamine compound in the presence of a catalytic agent.

BACKGROUND OF THE INVENTION

Polystyrene is a thermoplastic with many desirable characteristics. It is clear, transparent, readily colored and easily fabricated. The family of styrene polymers include polystyrene itself, copolymers of styrene with other vinyl monomers, polymers of derivatives of styrene and mixtures of polystyrene and styrene-containing copolymers with elastomers.

Common industrial methods for producing styrene typically include separation and purification processes such as distillation to remove unwanted impurities. Unfortunately, purification processes carried out at elevated temperatures result in an increased rate of undesired polymerization. The presence of oxygen, although virtually excluded in styrene distillation, will also promote polymerization of the monomer.

This polymerization results not only in loss of desired monomer end-product, but also in the loss of production efficiency caused by polymer formation and/or agglomeration of polymer on process equipment. Thermal polymerization of styrene monomer results in the formation of normal (i.e., linear) polymer. This resulting polystyrene polymer is characterized by its glassy and transparent appearance and its solubility in the styrene monomer and many organic solvents.

SUMMARY OF THE INVENTION

The present invention relates to a method for inhibiting the polymerization of vinyl aromatic monomers, particularly, styrene monomer under oxygen-free conditions utilizing a polymerization inhibiting compound and an effective amount of a catalytic agent.

Pursuant to the present invention, it has been found that effective inhibition of styrene polymerization is achieved under oxygen-free conditions using a hydroxylamine compound as the polymerization inhibiting compound and a phenylenediamine compound which acts as a catalyst in accelerating the reaction between the hydroxylamine and free radicals present in the monomer system.

DESCRIPTION OF THE RELATED ART

The compounds generally used commercially to prevent polymerization of vinyl aromatic monomers are of the dinitrophenolic type. For example, U.S. Pat. No. 4,105,506, Watson et al., teaches the use of 2,6-dinitro-p-cresol as polymerization inhibitor of vinyl aromatic compounds. U.S. Pat. No. 4,466,905, Butler et al., teaches that 2,6-dinitro-p-cresol and p-phenylenediamines will inhibit polymerization in the distillation column if oxygen is present. U.S. Pat. No. 4,774,374, Abruscato et al., teaches compositions and processes for inhibiting the polymerization of a vinyl aromatic compound employing an oxygenated species formed by the reaction of oxygen and a N-aryl-N'-alkyl-p-phenylenediamine. U.S. Pat. No. 4,720,566, Martin, teaches methods and compositions for inhibiting polymerization of acrylonitrile in the quench tower, no oxygen excluded, using a hydroxylamine compound and a phenyl p-phenylenediamine compound.

A variety of inhibitor compositions have been employed in styrene and other vinyl aromatic monomers to inhibit undesirable polymerization. Amongst others, agents that have been used include sulfur, p-benzoquinone, phenylenediamines, tert-butyl pyrocatechol, phenothiazine, hydroxylamines, nitrocompounds, and hindered phenols. However, many of these compounds present disadvantages such as high toxicity, instability and explosion hazard under elevated temperature, or insufficient efficacy under processing conditions (i.e., inhibitor requires oxygen to be effective). The present inventor has discovered a novel method for inhibiting vinyl aromatic monomer polymerization that avoids these problems associated with known inhibitors.

BRIEF DESCRIPTION OF THE DRAWINGS

FIG. 1 is a schematic diagram of one embodiment of the process of the present invention utilizing three process columns in a styrene monomer purification process.

DETAILED DESCRIPTION OF THE INVENTION

The present invention discloses methods for inhibiting the polymerization of vinyl aromatic monomers in an oxygen-free vinyl aromatic processing system containing a continuous feed stream of vinyl aromatic monomer, a continuous recycle stream returning to said feed stream, at least one process column, and a waste stream, the improvement comprising the steps of:

a) adding to said feed stream a sufficient polymerization inhibiting amount of a hydroxylamine compound;

b) adding as a catalyst a separate feed of a phenylenediamine compound to said feed stream in an amount sufficient to ensure that said phenylenediamine is present in said process column in a 1:9 to 9:1 weight ratio with said hydroxylamine compound;

c) replacing the amount of phenylenediamine compound physically removed from said system through said waste stream by adding an amount sufficient to compensate for the amount of said phenylenediamine compound removed and to maintain a constant level of said phenylenediamine compound in a 1:9 to 9:1 weight ratio with said hydroxylamine compound in said system.

The accompanying drawing is a simplified schematic flow sheet exemplifying the purification of vinyl aromatic monomer (styrene) in a low temperature vacuum distillation unit. A feed consisting mainly of ethylbenzene and styrene is fed through line 10 into a benzene/toluene fractionation column 11 where benzene and toluene are removed from a top line 13 to storage. The bottoms consisting mostly of ethylbenzene and styrene is fed through line 12 to an EB (ethylbenzene) recycle column 14. Ethylbenzene is removed through line 16 for return to the styrene synthesis facility. The EB recycle column bottoms consisting of styrene and high boiling impurities is fed through line 15 to a finishing column 17.

Finished styrene is removed to storage through line 19 and styrene, polymer and high boiling point compounds are passed through line 18 to a tar recovery system, 20 and 25. Tar bottoms from 20 are split through line 21, a continuous recycling stream which recycles to the feed line 10 and through line 23 to a tar recovery column 25. Tar waste exits the tar recovery column 25 through waste stream 24 and finished styrene flows through line 26 for storage.

In the process of the instant invention, the polymerization inhibiting compound, hydroxylamine compound, and the catalytic agent, phenylenediamine compound are added separately to the feed stream. The hydroxylamine compound can be added continuously or intermittently depending upon its consumption at inhibiting polymerization but is added to maintain an amount necessary to inhibit polymerization while the phenylenediamine is fed to the system, after the initial addition, to compensate for that amount of phenylenediamine physically removed via the waste stream. This ensures that the phenylenediamine, which is not consumed through inhibitory action, is maintained in the system in an amount necessary to act as a catalyst improving the inhibitory action of the hydroxylamine compound.

The hydroxylamine compound may be inputted at any point of the purification process to adjust for unexpected consumption. Thus, the hydroxylamine compound may be added at any time during the styrene monomer processing but it is preferably continuously added at the front of the processing system with the crude styrene in an amount necessary to inhibit styrene polymerization during the purification process.

The amount of phenylenediamine compound which is added is that sufficient to ensure its presence in the columns present in the purification apparatus. This amount is readily determined by sampling the columns' bottoms and analyzing by gas chromatography or a spectrophotometric analytical technique. The feed amount can then be used with the amount returned via the continuous recycle stream to determine the amounts of replacement phenylenediamine added to act as catalyst in further processing.

The amount of phenylenediamine compound removed with the waste stream is readily determined by sampling of the waste stream. A sufficient amount of phenylenediamine compound can then be fed through the feed stream to ensure that catalytic activity continues to occur in the processing system.

The present inventor has discovered that in the presence of a catalyst, phenylenediamine compound, polymerization is inhibited throughout the purification system. The hydroxylamine compound is more effective at inhibiting polymerization because the phenylenediamine compound improves the inhibiting action of the hydroxylamine compound more than in absence of any phenylenediamine compound. This results in a more efficient and less costly means for inhibiting the unwanted polymerization of styrene monomer and a lower amount of addition of hydroxylamine to supplement that used to inhibit polymerization.

The hydroxylamine compounds useful in this invention generally have the formula

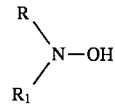

wherein R and $R_1$ are the same or different and are hydrogen, alkyl, aryl, alkaryl, aralkyl, or hydroxyalkyl groups and preferably have three to about twenty carbon atoms. The preferred hydroxylamine compound is bis-hydroxypropylhydroxylamine (HPHA).

The phenylenediamine compounds useful as catalysts in this invention generally have the formula

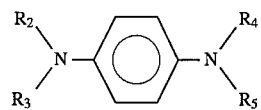

wherein $R_2$, $R_3$, $R_4$ and $R_5$ are the same or different and are hydrogen, alkyl, aryl, alkaryl or aralkyl groups having one to about twenty carbon atoms. The preferred phenylenediamine compound is N, N'-di-sec-butyl-p-phenylenediamine.

The phrase "oxygen-free processing conditions" is meant to define the substantially oxygen free condition that styrene monomers are typically processed under in systems such as purification and distillation. These systems and conditions generally have less than 2 ppm of oxygen present and preferably less than 1 ppm of oxygen per million parts styrene.

The term "catalytic" referring to the phenylenediamine compound defines that the phenylenediamine compound, under the oxygen-free conditions of hydroxylamine compound inhibiting styrene polymerization, improves the inhibiting effect of hydroxylamine while remaining unconsumed by the process. This catalytic effect results in the slower consumption of hydroxylamine compound while the concentration and amount of phenylenediamine compound remains the same.

As indicated, the styrene monomer and processing environment must be oxygen-free for the catalytic effects of the phenylenediamine compound to be realized. When oxygen is present, both the hydroxylamine compound and phenylenediamine compound will be consumed, albeit the phenylenediamine compound at a slower rate.

The amount of hydroxylamine compound utilized in the methods of the present invention is that amount which is necessary to inhibit polymerization of the styrene. This amount will vary according to the conditions under which the styrene is being processed, the amount of unreacted starting materials and distillable byproducts, and the temperature of the system.

Preferably, the total amount of hydroxylamine compound added to the styrene feed is from about 10 parts to about 10,000 parts per million parts styrene by weight. More preferably, the amount of hydroxylamine compound ranges from about 10 parts to about 2000 parts per million parts by weight styrene. The weight ratio of phenylenediamine added to this hydroxylamine compound added ranges from 1:9 to 9:1 and is preferably about 1:1 to about 1:2.

The hydroxylamine compound can be added to the styrene monomer by any conventional method. The hydroxylamine may be added as either a dispersion or as a solution using a suitable liquid carrier or solvent. Any solvent that is compatible with both the styrene monomer and phenylenediamine compound may be employed.

This invention will now be further described with reference to a number of specific examples which are to be regarded solely as illustrative, and not as restricting the scope of the invention.

EXAMPLES

In order to evaluate the improved polymerization inhibition when a phenylenediamine compound is employed as a catalyst, a styrene reflux under argon test was performed.

70 ml of freshly distilled uninhibited styrene was placed in a three-necked flask fitted with a condenser, a bubbler, and a rubber septum. The appropriate amount of phenylenediamine compound and hydroxylamine compound was added and argon was bubbled through the liquid at 15 ml/min with stirring from a magnetic stirrer. After 20 minutes the flask was immersed in a heated oil-bath. Argon bubbling continued through the test as samples were taken every 30 minutes. The amount of polystyrene formed was determined by methanol precipitation. Phenylenediamine concentration was determined by capillary gas chromatography using an internal standard. Hydroxylamine concentration was measured by HPLC with an electrochemical detector. The results of this testing are presented in Tables I and II.

TABLE I

Styrene (pure) under argon test at 120° C.
Treatment: 30 ppm hydroxypropylhydroxylamine (HPHA)
30 ppm N,N'-di-sec-butyl-p-phenylenediamine (PDA)

| Time (min) | Polymer Formed (mg/5 ml) | PDA Remaining (ppm) |
|---|---|---|
| 0 | 0 | 30 |
| 15 | 3 | 29 |
| 30 | 60 | 30 |
| 45 | 126 | 30 |
| 60 | 218 | 30 |

TABLE II

Styrene (pure) under argon test at 120° C.
Treatment: 75 ppm HPHA and 75 ppm PDA

| Time (min) | PDA (ppm) | HPHA (ppm) | Polymer Formed (mg/5 ml) |
|---|---|---|---|
| 0 | 75 | 75 | 0 |
| 45 | 75 | 78 | 0 |
| 90 | 75 | 74 | 0 |
| 135 | 75 | 62 | 0 |
| 180 | 75 | 47 | 64 |
| 225 | 75 | 56* | 224 |
| 270 | 75 | 41* | 648 |

*possible response variation in the detector.

This testing shows that polymerization is being inhibited while the amount of the catalyst, PDA, remains constant. This indicates that the PDA acts to activate or catalyze the reaction involved in inhibiting polymerization.

An experiment was utilized to demonstrate the effect of HPHA concentration of the onset of polymerization. The reflux under argon of Table II was repeated at 120° C. on pure styrene treated with 75 ppm of HPHA and 75 ppm of PDA. After 135 minutes of heating, the polymerization induction time under those conditions, an additional 35 ppm of HPHA was added. These results are shown in Table III.

TABLE III

| Time (min) | Polymer Formed (mg/5 ml) | PDA Remaining (ppm) | HPHA Remaining (ppm) |
|---|---|---|---|
| 0 | 0 | 75 | 75 |
| 45 | 0 | 74 | 78 |
| 90 | 0 | 75 | 74 |
| 135* | 0 | 75 | 62 |
| 180 | 0 | 75 | 47 |
| 225 | 0 | 75 | 48 |
| 270 | 0 | 75 | 41 |

*35 ppm of HPHA were added.

These results demonstrate that styrene polymerization is inhibited by HPHA while PDA is not consumed in the reactions. Satisfactory inhibition was achieved over an extended time period after the induction period by replenishing the supply of the inhibitor, HPHA, as needed.

Another polymerization test was run with no argon purging and only PDA added to the styrene results are shown in Table IV.

TABLE IV

Styrene (pure) without argon purging at 120° C.
Treatment: 100 ppm PDA

| Time (min) | Polymer Formed (mg/5 ml) | PDA Remaining (ppm) |
|---|---|---|
| 0 | 0 | 100 |
| 30 | 2 | 110 |
| 60 | 3 | 47 |
| 135 | 73 | not detected |
| 150 | 96 | not detected |

This testing shows that in the presence of oxygen, the phenylenediamine will inhibit polymerization but within one hour will totally be depleted. This demonstrates that when a known inhibitor, PDA, is employed alone in the presence of oxygen, it will inhibit polymerization until it is consumed. However, the same inhibitor when employed with HPHA in an oxygen-free system will catalyze and make more efficient the polymerization inhibition.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A method for inhibiting the polymerization of vinyl aromatic monomers in an oxygen-free vinyl aromatic processing system containing a continuous feed stream of vinyl aromatic monomer, a continuous recycle stream returning to said feed stream, at least one process column, and waste stream, comprising adding to said feed stream a sufficient polymerization inhibiting amount of a hydroxylamine compound, the improvement comprising the steps of:

a) using a phenylenediamine compound as a catalyst in said feed stream wherein said phenylenediamine compound will catalytically improve the polymerization inhibiting effect of said hydroxylamine compound; and b) maintaining the amount of said phenylenediamine compound in said process column in a weight ratio of 1:9 to 9:1 with said hydroxylamine compound.

2. The method as claimed in claim 1 wherein said hydroxylamine compound has the formula

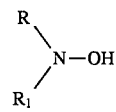

wherein R and $R_1$ are the same or different and are hydrogen, alkyl, aryl, alkaryl, aralkyl, or hydroxyalkyl groups, and have one to about twenty carbon atoms.

3. The method as claimed in claim 1 wherein said phenylenediamine compound has the formula

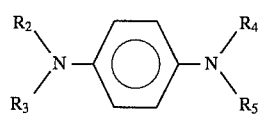

wherein $R_2$, $R_3$, $R_4$ and $R_5$ are the same or different and are hydrogen, alkyl, aryl, alkaryl or aralkyl groups having one to about twenty carbon atoms.

4. The method as claimed in claim 3 wherein said phenylenediamine compound is N,N'-di-sec-butyl-p-phenylenediamine.

5. The method as claimed in claim 1 wherein said hydroxylamine compound is added to said system in an amount ranging from 20 parts to about 10,000 parts per million parts styrene in said system.

6. The method as claimed in claim 1 wherein the weight ratio of phenylenediamine compound to hydroxylamine compound ranging from 1:1 to 2:1.

7. The method as claimed in claim 1 wherein said vinyl aromatic monomer is styrene.

8. The method as claimed in claim 1 wherein said system contains three process columns.

* * * * *